United States Patent
Spencer et al.

[11] 4,326,879
[45] Apr. 27, 1982

[54] 1-PHENOXY-4-PYRIDYLBUTANES AND DERIVATIVES

[75] Inventors: Homer K. Spencer, Randolph; Melvin M. Graben, Hackettstown, both of N.J.

[73] Assignee: Sandoz, Inc., E. Hanover, N.J.

[21] Appl. No.: 118,538

[22] Filed: Feb. 4, 1980

[51] Int. Cl.³ .................. A01N 43/40; C07D 213/64; C07D 213/65
[52] U.S. Cl. ....................... 71/94; 546/268; 546/301; 546/302; 542/413
[58] Field of Search ............... 542/413; 546/301, 302, 546/268

[56] References Cited

U.S. PATENT DOCUMENTS

| | | | |
|---|---|---|---|
| 3,814,774 | 6/1974 | Whitaker et al. | 546/302 |
| 4,105,435 | 8/1978 | Nishiyama et al. | 546/302 |
| 4,213,774 | 7/1980 | Schurter et al. | 71/94 |

Primary Examiner—Alan L. Rotman
Attorney, Agent, or Firm—Gerald D. Sharkin; Richard E. Vila

[57] ABSTRACT

Herbicides are of the formula

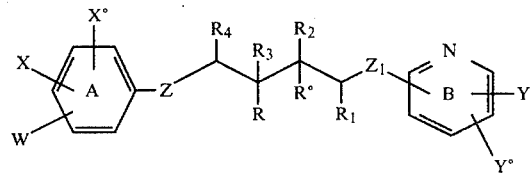

wherein
W is fluoro, bromo, chloro or $CF_3$,
each of X and X° is independently H, fluoro, chloro, bromo, $C_1$-$C_4$ alkyl, $C_1$-$C_4$ alkoxy, $CF_3$ or nitro,
Z and $Z_1$ are independently oxygen or sulfur, with the proviso that at least one is oxygen,
each of Y and Y° is independently H, fluoro, chloro, bromo, $C_1$-$C_4$ alkyl, $C_1$-$C_4$ alkoxy, $CF_3$ or nitro,
$R_1$ and $R_4$ are independently H, $C_1$-$C_4$ alkyl and —$COOR_5$ wherein $R_5$ is H or $C_1$-$C_4$ alkyl,
$R_2$ and $R_3$ are independently H, $C_1$-$C_5$ alkyl, fluoro, chloro, bromo or hydroxy, and
R and R° are independently H or $C_1$-$C_3$ alkyl or both together form a covalent bond or an epoxy bridge (—O—), with the further proviso that no two adjacent ring members in either Rings A or B are from the group of t-butyl, t-butoxy and $CF_3$.

15 Claims, No Drawings

1-PHENOXY-4-PYRIDYLBUTANES AND DERIVATIVES

The present invention relates to bis-phenoxy hydrocarbon derivatives, their use as herbicides and herbicidal compositions containing the same.

The compounds of the present invention may be represented structurally by the following formula I:

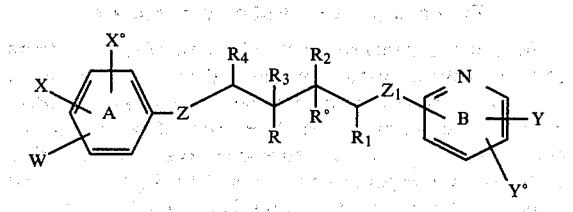

wherein
W is fluoro, bromo, chloro or CF$_3$,
each of X and X° is independently H, fluoro, chloro, bromo, C$_1$-C$_4$ alkyl, C$_1$-C$_4$ alkoxy, CF$_3$ or nitro,
Z and Z$_1$ are independently oxygen or sulfur, with the proviso that at least one is oxygen,
each of Y and Y° is independently H, fluoro, chloro, bromo, C$_1$-C$_4$ alkyl, C$_1$-C$_4$ alkoxy, CF$_3$ or nitro,
R$_1$ and R$_4$ are independently H, C$_1$-C$_4$ alkyl and —COOR$_5$ wherein R$_5$ is H or C$_1$-C$_4$ alkyl,
R$_2$ and R$_3$ are independently H, C$_1$-C$_5$ alkyl, fluoro, chloro, bromo or hydroxy, and
R and R° are independently H or C$_1$-C$_3$ alkyl or both together form a covalent bond or an epoxy bridge (—O—),
with the further proviso that no two adjacent ring members in either Rings A or B are from the group of t-butyl, t-butoxy and CF$_3$.

The compounds of the formula I may be produced in a process (a) by condensing a compound of the formula II or II':

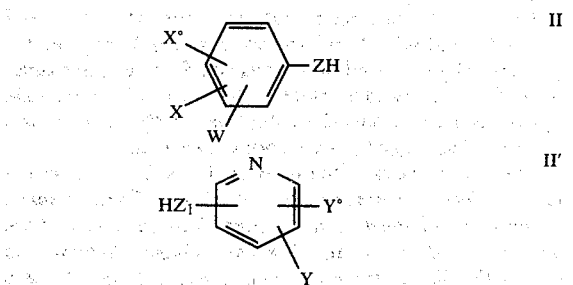

wherein W, X, X°, Y, Y°, Z and Z$_1$ are as above defined, with an aliphatic hydrocarbon derivative of the formula III:

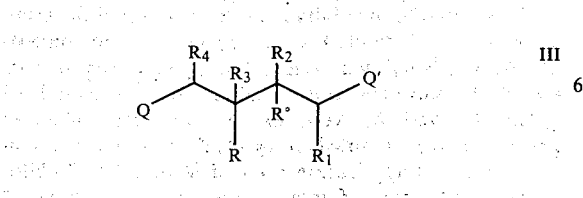

wherein
R, R$_1$, R$_2$, R$_3$, R$_4$ and R° are as above defined and
Q is a leaving group displaceable under phenolic (phenol or thiophenol) condensing conditions, and
Q' is either (i) a leaving group displaceably under phenolic condensing conditions or (ii) a radical of the formula B or B':

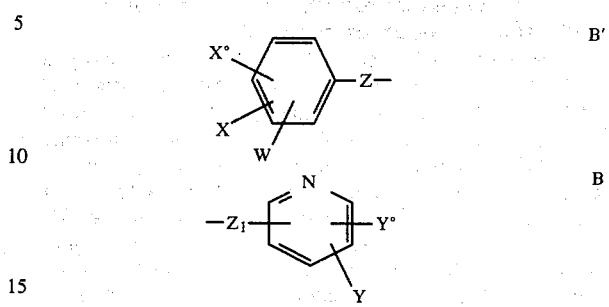

wherein W, X, X°, Y, Y°, Z and Z$_1$ are as above defined with the proviso that at least one compound from the group of compounds III with the B' radical and compounds II and at least one compound from the group of compounds III with the B radical and compounds II' be employed.

The compounds of the formula I in which R and R° are both H may also be produced in a process (b) by reducing a compound of the formula I':

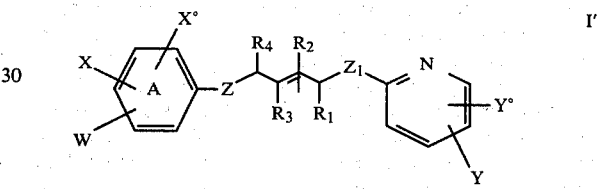

wherein W, X, X°, Y, Y°, Z, Z$_1$, R$_1$, R$_2$, R$_3$ and R$_4$ are as above defined, with an alkene reducing system in accordance with known procedures.

The compounds of the formula I in which R° and R form an epoxy bridge, ie. the compounds of the formula I'':

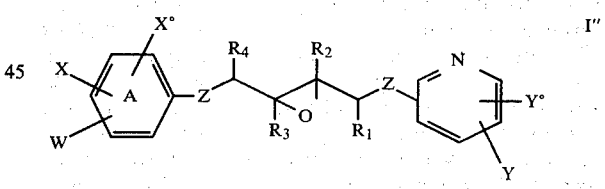

wherein W, X, X°, Y, Y°, Z, Z$_1$, R$_1$, R$_2$, R$_3$ and R$_4$ are as above defined, may be produced by epoxylating in a process (c) a compound of the formula I', above stated, in accordance with known procedures.

Process (a) may be effected in an appropriate organic solvent, e.g. dimethylformamide, in the presence of an alkali, eg. potassium hydroxide, or in an aqueous/organic two phase system, e.g. water/toluene, in the presence of an alkali, e.g. potassium hydroxide, and a phase transfer catalyst, e.g. benzylammonium chloride. The reaction is preferably effected in an organic solvent in the presence of a base, e.g. an alkali such as KOH, alkali metal carbonate such as Na$_2$CO$_3$ or a metal hydride such as NaH. The reaction may be effected over a wide range of temperatures, e.g. 15°–100° C. Typical leaving groups for Q and Q' are chloro, bromo, iodo, methanesulfonate and p-toluenesulfonate. As will be appreciated, the relative amounts of the reactants will depend on the nature of the group Q'. When Q' is a leaving group, more or less equal molar mixtures of a compound II and II' totally 2 moles are reacted with 1 mole of the compound III but the resulting mixtures make such procedure much less practical.

It is accordingly generally preferred to employ a compound III in which Q' is a radical of the formula B or B', and the reactants are then preferably condensed in equimolar proportions. A compound of the formula III in which Q' is a radical B or B' is similarly preferably employed when producing compounds of the formula I which are assymmetrical by reason of the compound III itself being assymmetrical. In general, it is more preferred to employ a compound III in which Q' is a radical B' and thus react the same with a compound II'.

Separation of mixtures that may be formed in process (a) may be effected by known procedures such as chromatography, fractional crystallization and the like, particularly gas chromatography.

Process (b) may be effected in a solvent such as ethyl acetate with an alkene reducing system or agent such as by catalytic hydrogenation, e.g. employing palladium, platinum or Raney nickel as catalyst, or diborane. The reaction may be carried out at, e.g. 0° C. to 100° C., and is preferably effected at room temperature.

Process (c) may be effected in a solvent such as acetic acid, chloroform or methylene chloride, employing a peracid, e.g. peracetic acid or m-chloroperbenzoic acid, as epoxylating agent at temperatures of, e.g. 0° C. to 100° C.', and preferably at room temperature.

The compounds of the formulae II and III are generally known and may be prepared as described in the literature for the known compounds and by established procedures from known materials where not specifically heretofore known.

The compounds of the formula III in which Q' is a radical of the formula B or B' may, for example, be produced by reacting 1 mole of a compound III in which Q' is a leaving group with one mole of a compound of the formula II or II' in an organic solvent for both the reactants and desired product. A manipulative type procedure for preparing the compounds of the formula III in which Q' is a radical of the formula B or B' involves dissolving 1 mole of a compound III in which Q' is a leaving group in an aqueous medium along with 1 mole of a compound of the formula II or II', and reacting the same at an appropriate temperature, eg. 15°–100° C., whereby the resulting compound of the formula III in which Q' is a radical of the formula B or B' may be dispelled from solution without further substantial reactions that would undesirably lead to the replacement of the Q leaving group. Mixtures of the product compounds III that may result from such reactions, such as mixtures of position isomers by reason of the starting compound III being assymmetrical, may be separated by established procedures, eg. gas chromatography. In general, the separation to avoid position isomers that may be present in the various reaction sequences described herein, when desired, preferably is effected at this time, ie. before the compound III is further reacted with a compound II or II'.

Geometric isomerism is possible in compounds I in which R° and R form a covalent bond or are epoxy bridge, and in intermediates and starting materials therefor, as will be evident. The particular geometric forms of such intermediates and starting materials are generally unaffected by the reaction conditions described herein and will appear in the final products.

When mixtures of geometric isomers are produced, it is, as a practical matter, generally preferred to employ such mixtures as such in the herbicide method and compositions of the invention, even though separation may be effected by known procedures.

The compounds of formula I are useful as herbicides as indicated in the following Tests.

TEST 1

Pre-emergence Greenhouse Treatment

Seed dishes measuring 30×40 cm are filled to a depth of 6 cm with a mixture of peat culture substrate no. 1 (obtainable from Torfstreuverbant G.m.b.H., 29 Oldenberg, Germany) and sand. The exposed surface of the peat culture and sand mixture is sprayed with 50 ml of a test solution equivalent to 1.0 and 5.0 kg/hectare and 6 species of seed are then sown in each dish. The number of seeds sown for each plant species depends on the seed germination potential and also the initial growth size of the particular seed plant. After sowing of the seeds, the treated surface is covered with a thin layer about 0.5 cm deep of the peat culture and sand mixture. The prepared seed dishes are kept for 28 days at a temperature of 20° to 24° C. and 14 to 17 hours normal summer day daylight each day.

Determination of the herbicidal effect of the particular herbicide is made after the 28 day period. The determination involves a visual evaluation of the degree and quality of damage to the various seed plants.

TEST 2

Post-emergence Greenhouse Treatment

A procedure similar to that of the pre-emergence test described above is followed, except that the 50 ml of herbicide solution is applied when the seed plants are at the 2–4 leaf stage. In order that uniform treatment of various seed plants may be effected at a time when each of the plant species has reached the 2–4 leaf stage, the various seed species are sown in time staggered relationship.

As with the pre-emergence test, the prepared seed dishes treated with herbicide are kept for 28 days under the greenhouse conditions described. The determination of the herbicidal effect of the particular herbicide again involves a visual evaluation of the degree and quality of damage to the various seed plants.

The plant species involved in Tests 1 and 2 above were as follows: *Amaranthus retroflexus, Capsella bursa pastoris, Apera spica venti, Chenopodium album, Galium aparine, Stellaria media, Senecio vulgaris, Echinochloa crus galli, Alopecurus myosuroides, Avena fatua, Agrostis alba.*

Each of the compounds listed in the following Examples exhibits a significant herbicidal effect in both of the above Tests, especially at the higher dosages.

The desired herbicidally effective amount of the compounds of the formula I to be employed in the combatting of weeds will vary depending upon known factors such as the particular compound employed, the mode of application and the weed species to be controlled. In general, however, satisfactory total weed control may be obtained at application rates of from 1.0 to 20 kilograms per hectare of treated area. The compounds I may be applied to the area to be treated by standard procedures and either pre-emergence or post-emergence, but generally exhibit much greater potency in post-emergence application which is a preferred contemplated mode of application at rates preferably of 1.0 to 12 kilograms per hectare. The compounds of the formula I have also been found to exhibit a selective action, particularly in post-emergence application, with regard to certain crops such as wheat, corn and carrots. Hence, other preferred aspects of the invention involve the combatting of weeds, especially by post-emergence application, in a wheat, rice, corn or carrot crop locus, particularly a wheat or corn locus, and especially a wheat locus. Application rates for such selective use are indicated to be from 1.0 to 10 kilograms per hectare generally with rates of from 2.0 to 5.0 kilograms per hectare preferably employed in post emergence application. The emergence time referred to above is with respect to the weeds. In the preferred post emergence selective use the compounds I may be applied pre emergence the crop but it is generally preferred to effect the application post emergence both the weeds and crop.

The compounds may be employed as herbicidal compositions in association with biologically inert herbicide carriers. Such compositions also form part of the present invention.

Herbicidal compositions may be employed in either solid or liquid application forms. Solid forms, e.g. dusting forms and granulates, may be produced by mixing or impregnating solid herbicide carriers such as diatomaceous earth, kaolin, talc, chalk, limestone and cellulose powder, with the compounds.

Additives may be employed in the herbicidal composition. Typical of such additives are wetting and dispersing agents, e.g. the condensation product of formaldehyde with naphthalene sulphonate, and alkyl benzene sulphonates, adhesion imparting agents, e.g. dextrin, and emulsion stabilizers, e.g. ammonium caseinate. Such additives are suitable for incorporation into, e.g. a wettable powder form of composition or together with suitable solvents, e.g. hydrocarbons such as benzene, toluene, xylene, tetrahydronaphthalene, alkylated naphthalenes, kerosene, aromatic petroleum hydrocarbon fractions (e.g. commercial product Shellsol AB having b.pt. range 187°–213° C.), ketones such as isophorone, acetone, cyclohexanone, diisobutylketone and methylethylketone, alcohols such as isopropanol, ethanol, and methylcycloyexanol, chlorinated hydrocarbons such as tetrachloroethylene, ethylene chloride or trichloroethylene, to form emulsion concentrates.

The herbicidal compositions may contain, aside from a compound of formula I as active agent, and an inert herbicide carried, other active agents, such as herbicides.

Concentrate forms of composition generally contain between 2 and 80%, preferably between 2 and 50 %, by weight of a compound of formula I as active agent.

Application forms of composition generally contain between 0.01 and 10%, by weight of a compound of formula I as active agent.

Specific Examples of herbicidal compositions will now be described.

EXAMPLE A

Wettable Powder

26 Parts by weight of a compound of formula I, e.g. m-trifluoromethylphenoxy butane pyridyl-3 ether are sprayed on a mixture of 66 parts of diatomaceous earth, 3 parts of sodium lauryl sulphate and 5 parts of lignin sulfonate to obtain a powder which is ground in a mill and thereafter mixed until a homogeneous mixture is obtained.

EXAMPLE B

Emulsion Concentrate

25 Parts of a compound of formula I, m-trifluoromethylphenoxy butane pyridyl-3 ether, 65 parts of xylene and 10 parts of the mixed reaction product of an alkylphenol with ethylene oxide and calciumdocecylbenzene sulphonate are thoroughly mixed until a homogeneous solution is obtained. The resulting emulsion concentrate is diluted with water before use.

EXAMPLE C

Granulate 5 kg of a compound of formula I, e.g. m-trifluoromethylphenoxy butane pyridyl-3 ether, are dissolved in 25 l methylene chloride. The solution is then added to 95 kg of granulated attapulgate (mesh size 24/48 mesh/inch) and thoroughly mixed. The solvent is then evaporated off under reduced pressure with warming.

The preferred compounds of the formula I have one or more and more preferably all of the following features: (A) W being $CF_3$ at the m-position of Ring A; (B) X and X° both being hydrogen; (C) R being H or $C_1$–$C_3$ alkyl, eg. ethyl with $R_1$, $R_2$, $R_3$ and $R_4$ all being H; (D) Z and $Z_1$ both being oxygen; (E) the pyridyl Ring B being attached to its ether linkage at the 3-position of the pyridyl ring; and (F) Y being H and Y° being H, chloro or $C_1$–$C_2$ alkyl.

The following examples are given for purposes of illustration only.

EXAMPLE 1 m-trifluoromethylphenoxy butane pyridyl-3 ether

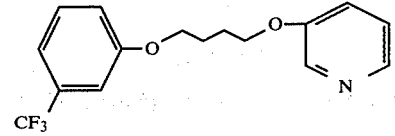

To 60 ml. of dimethylformamide is added 1.73 g. of potassium hydroxide and 2.35 g. 3-hydroxypyridine followed by stirring for 30 minutes. There is then added 7.34 g. of 1-bromo-4-trifluoromethylphenoxy butane followed by stirring for an additional 2 hours at room temperature. The resulting reaction mixture is poured into water and extracted with ether followed by evaporation in vacuo to obtain an oil which is chromatographed over 100 g. of silica gel while eluding with hexane/ethyl acetate (85:15) to m-trifluoromethylphenoxy butane pyridyl-3 ether as an oil, $N_D^{20}$ 1.5131.

EXAMPLE 2 o,p-dichlorophenoxy butane pyridyl-2 thioether

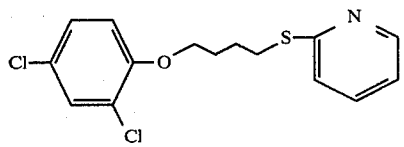

A mixture of 3.75 g. of 1-chloro-4-(o,p-dichlorophenoxy) butane, 1.65 g. of 2-mercaptopyridine, 1.0 g.

of potassium hydroxide and 10 ml. of dimethylformamide is stirred for 15 hours at room temperature, poured onto water and extracted with ether. The ether layer is then washed with water and evaporated to a yellow oil which is distilled (200° C./0.3 mm) to obtain o,p-dichlorophenoxy butane pyridyl-2 thioether as a yellow oil.

EXAMPLE 3

1-(pyridyl-3-oxy)-3-ethyl-4-(m-trifluoromethylphenoxy)-2-butene

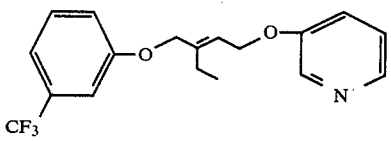

To 30 ml. of dimethylformamide is added 1.9 g. of 3-hydroxypyridine and 1.4 g. of potassium hydroxide followed by stirring at room temperature until the reagents are dissolved (about 30 minutes). To the resulting solution is added dropwise 6.5 g. of 1-bromo-3-ethyl-4-(m-trifluoromethylphenoxy)butene-2 followed by stirring at room temperature for 2.5 hours. The resulting reaction mixture is poured into water and following extraction with ether the organic phase is washed with water and evaporated in vacuo to an oil which is then chromatographed over silica gel employing hexane/ethyl acetate as eluant to obtain 1-(pyridyl-3-oxy)-3-ethyl-4-(m-trifluoromethylphenoxy)-2-butene as an oil.

EXAMPLE 4

1-(pyridyl-3-oxy)-3-ethyl-4-(m-trifluoromethylphenoxy)butane

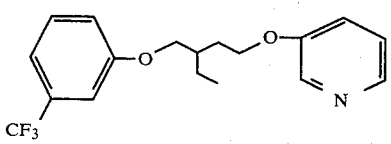

A hydrogenation flask is charged with 22 ml. of ethyl acetate, 2.9 g. of 1-(pyridyl-3-oxy)-3-ethyl-4-(m-trifluoromethylphenoxy)-2-butene and a catalytic amount of palladium on charcoal. Hydrogen is introduced while stirring the mixture until no additional hydrogen uptake is observed. The excess hydrogen is removed by suction and replaced by nitrogen. The flask is then opened, the reaction mixture filtered to remove catalyst and the solvent evaporated in vacuo to obtain an oil which is chromatographed over silica gel while eluding with hexane with a minor portion of ethyl acetate to obtain 1-(pyridyl-3-oxy)-3-ethyl-4-(m-trifluoromethylphenoxy)ethane as an oil.

EXAMPLE 5

1-(pyridyl-3-oxy)-4-(m-trifluoromethylphenoxy)-2,3-epoxy butane

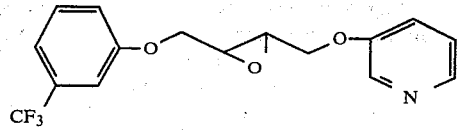

A solution of 7.5 g. of 1-(pyridyl-3-oxy)-4-(m-trifluoromethylphenoxy)-2-butene in 20 ml. of methylene chloride is added at room temperature to a solution of 4 g. of m-chloroperbenoic acid in 50 ml. of methylene chloride. The resulting mixture is stirred for 4.5 days at room temperature and then poured into 100 ml. of saturated aqueous sodium sulphite. The resulting liquid is then extracted with ether and the ether extract washed twice with saturated aqueous sodium carbonate and once with saturated aqueous sodium chloride. After drying with anhydrous sodium sulphate the ether is removed in vacuo and the resulting oil chromatographed over silica gel while eluding with chloroform to obtain 1-(pyridyl-3-oxy)-4-(m-trifluoromethylphenoxy)-2,3-epoxy butane as an oil.

EXAMPLE 6

Following the procedure of Examples 1-3 the following additional compounds of the invention are prepared.

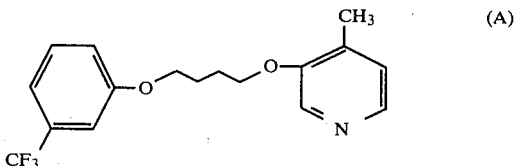
(A)

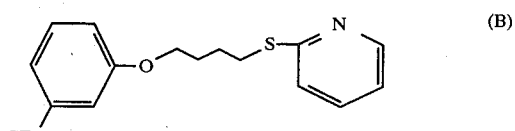
(B)

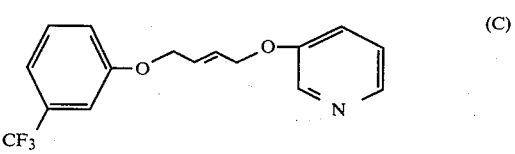
(C)

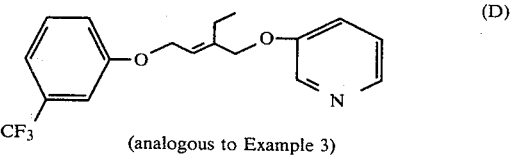
(D)
(analogous to Example 3)

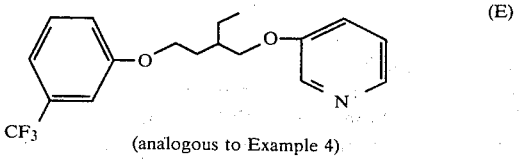
(E)
(analogous to Example 4)

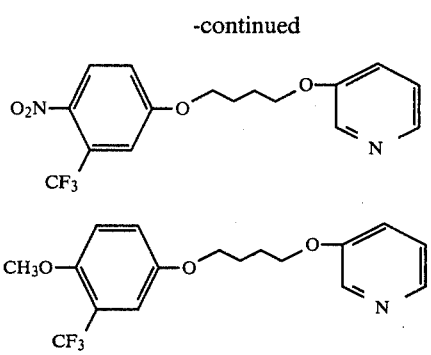

(F)

EXAMPLE 7

1-bromo-2-ethyl-4-(m-trifluoromethylphenoxy)butene-2 (and 3-ethyl isomer).

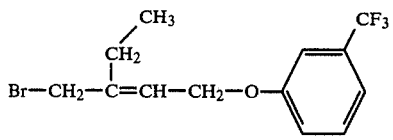

To a flask charged with 7.26 g. of 1,4-dibromo-2-ethylbutene-2 and 10 ml of water and heated to 50° C. is added slowly over the course of 10 minutes a solution of 4.86 g. of m-trifluoromethylphenol and 2.3 g. of sodium hydroxide in 12 ml of water. The resulting mixture is heated at 80° C. for 6 hours and the resulting organic phase extracted twice with chloroform, and the combined extracts washed with water. After filtering over Celite and silica gel, the chloroform system is evaporated in vacuo to an oil constituting an 86:14 mixture of the isomers 1-bromo-2-ethyl-4-(m-trifluoromethylphenoxy)butene-2 and 1-bromo-3-ethyl-4-(m-trifluoromethylphenoxy)butene-2, each of the position isomers having a cis:trans ratio of 20:80. The isomeric mixture thus obtained is subjected to gas chromatography to separate and obtain the individual isomers in substantially pure form without variation of their cis:trans ratio for use as starting materials in the foregoing examples.

What is claimed is:

1. A compound of the formula:

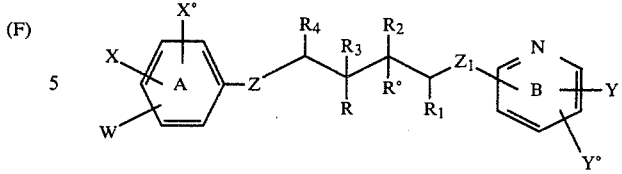

(G)

wherein
W is $CF_3$ in the meta position of Ring A
each of X and X° are H,
Z and $Z_1$ are independently oxygen or sulfur, with the proviso that at least one is oxygen,
Y is H,
Y° is H, Cl or $C_1$–$C_2$ alkyl,
$R_1$, $R_2$ $R_3$ and $R_4$ are H.

2. A compound of claim 1 in which Y is H and Y° is H, chloro or $C_1$–$C_2$ alkyl.

3. A compound of claim 1, in which Z and $Z_1$ are each oxygen.

4. The compound of claim 1 which is m-trifluoromethylphenoxy butane pyridyl-3 ether.

5. The compound of claim 1 which is 1-(pyridyl-3-oxy)-3-ethyl-4-(m-trifluoromethylphenoxy)butane.

6. The method of combatting weeds comprising applying to a weed locus a herbicidally effective amount of a compound of claim 1.

7. The method of claim 6 in which the pyridyl Ring B is attached to its ether linkage at the 3-position of said pyridyl ring.

8. The method of claim 6 in which the compound is m-trifluoromethylphenoxy butane pyridyl-3 ether.

9. The method of claim 6 in which the compound is 1-(pyridyl-3-oxy)-3-ethyl-4-(m-trifluoromethylphenoxy)butane.

10. The method of claims 6, 7, 8 or 9 in which weeds are selectively combatted in a crop locus of a crop selected from the group consisting of wheat, rice, corn and carrots by applying to said crop locus an amount of the compound herbicidally effective against such weeds but insufficient to substantially damage the crop.

11. The method of claim 10 in which Z and $Z_1$ are each oxygen.

12. The method of claim 10 in which Z and $Z_1$ are each oxygen and weeds are combatted in a wheat crop by application of the compound post emergence the wheat.

13. The method of claims 6, or 7, in which Z and $Z_1$ are each oxygen.

14. An agricultural composition for combatting weeds comprising an inert agriculturally acceptable carrier and a herbicidally effective amount of a compound of claim 1.

15. The compound which is o,p-dichlorophenoxy butane pyridyl-2-thio ether.